United States Patent [19]

Fortney

[11] Patent Number: 5,111,810

[45] Date of Patent: May 12, 1992

[54] THERAPEUTIC THERMAL WRAP KIT

[76] Inventor: Donald Fortney, P.O. Box 195, Clarksville, Md. 21029

[21] Appl. No.: 625,531

[22] Filed: Dec. 11, 1990

[51] Int. Cl.⁵ .............................................. A61F 7/00
[52] U.S. Cl. ................................ 128/402; 128/399; 128/400; 128/165; 602/2
[58] Field of Search ............... 128/399, 400, 402, 403, 128/77, 165; 62/530; 165/46

[56] References Cited

U.S. PATENT DOCUMENTS

| | | | |
|---|---|---|---|
| 298,969 | 12/1988 | Pryor . | |
| 1,970,081 | 8/1934 | Eisendrath | 128/400 |
| 3,545,230 | 12/1970 | Morse | 62/530 |
| 3,614,875 | 10/1971 | McCallun | 62/530 |
| 3,736,769 | 6/1973 | Peterson | 62/530 |
| 3,780,537 | 12/1973 | Spencer | 62/530 |
| 3,885,403 | 5/1975 | Spencer | 62/530 |
| 3,889,684 | 6/1975 | Lebold | 128/402 |
| 3,900,035 | 8/1975 | Welch et al. | 128/402 |
| 3,974,658 | 8/1976 | Starrett | 62/530 |
| 3,998,072 | 12/1976 | Shaw | 62/530 |
| 4,050,264 | 9/1977 | Tanaka | 62/530 |
| 4,055,188 | 10/1977 | Pelton | 128/402 |
| 4,092,982 | 6/1978 | Salem | 128/82.1 |
| 4,243,041 | 1/1981 | Paul | 128/402 |
| 4,326,533 | 4/1982 | Henderson | 128/402 |
| 4,344,303 | 8/1982 | Kelly, Jr. | 62/530 |
| 4,381,025 | 4/1983 | Schooley | 128/402 |
| 4,393,975 | 7/1983 | Moore | 62/530 |
| 4,404,820 | 9/1983 | Romaine | 62/530 |
| 4,527,566 | 7/1985 | Abare | 128/402 |
| 4,586,506 | 5/1986 | Nangle | 128/403 |
| 4,592,358 | 6/1986 | Westplate | 128/402 |
| 4,625,729 | 12/1986 | Roney | 128/402 |
| 4,652,141 | 3/1987 | Arai | 368/278 |
| 4,671,267 | 6/1987 | Stout | 128/156 |
| 4,676,247 | 6/1987 | Van Cheve | 128/402 |
| 4,688,572 | 8/1987 | Hubbard et al. | 128/402 |
| 4,741,176 | 5/1988 | Johnson et al. | 62/530 |
| 4,793,149 | 12/1988 | Riche | 62/530 |
| 4,832,031 | 5/1989 | Last | 128/402 |
| 4,856,651 | 8/1989 | Francis, Jr. | 206/219 |
| 4,905,997 | 3/1990 | Last | 273/29 A |
| 4,905,998 | 3/1990 | Last | 273/29 A |

OTHER PUBLICATIONS

*Tennis Magazine*, Feb. 1986, p. 146.

*Primary Examiner*—Richard J. Apley
*Assistant Examiner*—Linda C. Dvorak
*Attorney, Agent, or Firm*—Oblon, Spivak, McClelland, Maier & Neustadt

[57] ABSTRACT

The present invention relates to a therapeutic thermal wrap kit to be used for treatment of body discomfort, such as muscle and/or ligament stress (e.g., tennis elbow, tendonitis of the knee, chronic sore shoulder, etc.). The therapeutic thermal wrap kit comprises a thermal compress, a holder for the compress, a container around which the holder containing the thermal compress is wrapped, and an insulated bag in which the assembled components are placed and transported. The container may contain a substance, liquid at 25° C. which, along with the thermal compress, can be thermally adjusted to a temperature of from −20° to 120° C. The kit remains at a therapeutically effective temperature for at least 10 hours due to the synergy of the four elements in combination. When needed, the holder containing the compress and the container are removed from the insulated bag, the container is then separted from the holder, and the compress is applied to the affected body part using the holder. Therapeutic effectiveness is immediate, since the warp is at an effective temperature and is easily conformed to the shape of the affected body part.

22 Claims, 8 Drawing Sheets

THERAPEUTIC THERMAL WRAP KIT

BACKGROUND OF THE INVENTION

It is commonly accepted medical opinion that body parts stressed during exercise, such as the elbow or knee, respond well to the immediate application of cold. Oftentimes, persons suffering from muscle or ligament stress will wait until they return home to apply thermal treatment. For the affected member, waiting for many minutes or perhaps hours causes the application of thermal treatment to lose much of its therapeutic value.

In the past, persons suffering from chronic stress of muscles or ligaments who have attempted to bring some form of thermal treatment with them to the site of the exercise activity have resorted to ice or a commercially available thermal compress. In the case of ice, it is heavy, awkward and messy to use. It does not easily conform to the shape of the body part and quickly melts. In the case of the thermal compress, when it is removed from an external source of heat or cold, it quickly returns to ambient temperatures.

Many individuals suffer from chronic discomfort in one or more extremities such as that caused by muscle injury, tendinitis, or permanent ligament damage. The typical amateur athlete, who desires the benefits of exercise, but does not necessarily wish to participate in organized, competitive athletics, and thus, does not have professional medical or training help readily available, is often discouraged from exercising because of the discomfort caused by minor, yet seemingly chronic, injuries. Surprisingly, no effective, portable devices for convenient, immediate thermal treatment of exercise-related injuries are commercially available in spite of the long-felt need for just such a device.

SUMMARY OF THE INVENTION

With the invention therapeutic thermal wrap kit, a user has a wrap which both retains its altered temperature state for long periods of time and easily conforms to the affected body part. It can be applied both periodically during and immediately after the cessation of the exercise, thus reducing the likelihood of swelling, stiffening, pain, and similar discomforts.

The invention kit is simple to use and manufacture. It comprises a conventional thermal compress and a container of liquid, both of which are able to be thermally altered over a wide range of temperatures and retain a desired temperature for a long period of time, a holder for the thermal compress to apply the compress to a body part snugly and comfortably, and an insulated, fitted carrying bag for ease of portability and convenience of the thermal wrap.

Accordingly, it is an object of the present invention to provide a therapeutic thermal wrap kit, comprising:
(A) a holder comprising
  (1) at least two sheets of material peripherally attached to each other, said sheets forming a pocket, and
  (2) fastening means attachable to the outside of said holder for securing said holder to an affected body part;
(B) a thermal compress, which is inserted into said pocket;
(C) a container, around which the holder containing the thermal compress is wrapped; and
(D) an insulated bag, into which the assembled holder, thermal compress and container are placed, thus forming the therapeutic thermal wrap kit.

It is a further object of this invention to provide a portable therapeutic thermal wrap kit which is able to maintain a therapeutically effective temperature for at least ten hours away from external sources of heat or cold.

It is a further object of the present invention to provide a method for the treatment of body discomfort, comprising:
(A) adjusting the temperature of a thermal compress and a container containing a substance to a temperature of from $-20°$ to $120°$ C., said substance being liquid at $25°$ C.;
(B) placing said thermal compress in a holder comprising
  (1) at least two sheets of material peripherally attached to each other, said sheets forming a pocket, and
  (2) fastening means attachable to the outside of said pocket;
(C) securing said holder containing said thermal compress around said container;
(D) placing said secured holder in an insulated bag, forming a therapeutic thermal wrap kit;
(E) removing said secured holder from said insulated bag;
(F) separating said secured holder from said container; and
(G) securing said holder containing said thermal compress to a body part experiencing discomfort.

It is a further object of this invention to provide a method for the treatment of body discomfort in which the invention therapeutic thermal wrap kit, after assembly, is transported to a remote location prior to use.

BRIEF DESCRIPTION OF THE DRAWINGS

A more complete appreciation of the invention and many of the attendant advantages thereof will be readily obtained as the same become better understood by reference to the following description when considered in connection with the accompanying drawings, wherein.

DESCRIPTION OF THE PREFERRED EMBODIMENTS

Figure 1:
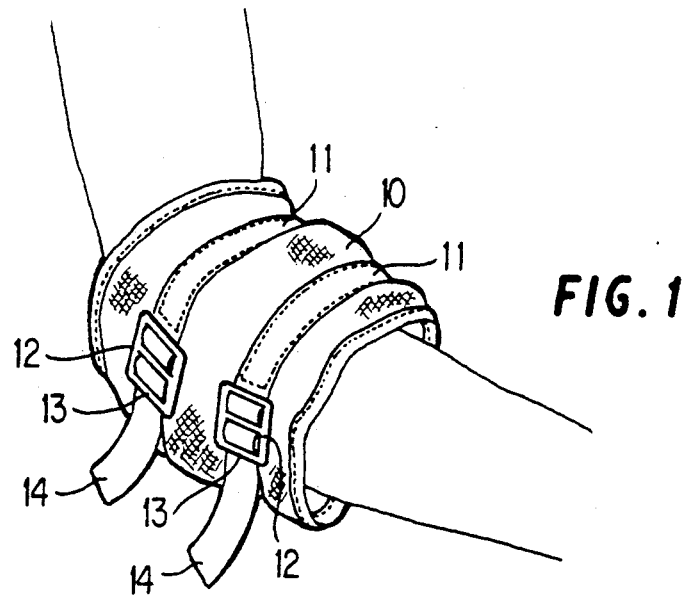
FIG. 1 is a perspective view of a holder containing a thermal compress of the present invention secured around an elbow, exemplifying the final step of the present method.

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 1 shows an embodiment of the present holder 10 (outside surface) containing the thermal compress (not seen) and fastening mean comprising straps 11 and buckles 12 fitted on a human elbow. The embodiment shown in FIG. 1 is effective for either heat therapy and cryotherapy of the forearm, elbow, upper arm, knee, ankle, foot or other body part around which the fastening means comprising straps 11 and buckles 12 can secure the holder 10 containing the thermal compress.

The particular shape and relative size of the embodiment shown in FIG. 1 is not intended to be limiting in any way. For example, a similar embodiment comprising two or three thermal compresses and a holder about twice as wide and about one to one-and-one-half times as long as the embodiment shown in FIG. 1 will be effective for heat therapy and cryotherapy of the knee, lower leg, upper leg, or other body part around which similar or different fastening means can secure the holder containing the thermal compresses. Another embodiment, smaller in size, can be adapted for heat therapy and cryotherapy of the wrist and hand.

To secure the holder 10 containing the thermal compress as shown in FIG. 1, the edge 13 of the buckle is pulled away from the holder 10 to loosen the straps 11. The arm is placed through the holder 10, and while using the arm to apply pressure to the holder 10 (for example, by squeezing the holder 10 between the arm and body, or resting the arm on a stationary object), the free hand pulls on the ends 14 of the straps 11 to secure the holder 10 to the arm. Alternatively, hook-and-loop fastening means (VELCRO) permanently attached to elastic straps can be employed, as well as strap-and-buckle fastening means other than that shown in FIG. 1. Although there is no general requirement that the fastening means be permanently attached to the outside of the holder 10, it is preferred that for embodiments designed for thermal treatment of extremities that the fastening means be securely attached to the outside of the holder 10.

Figure 2A:
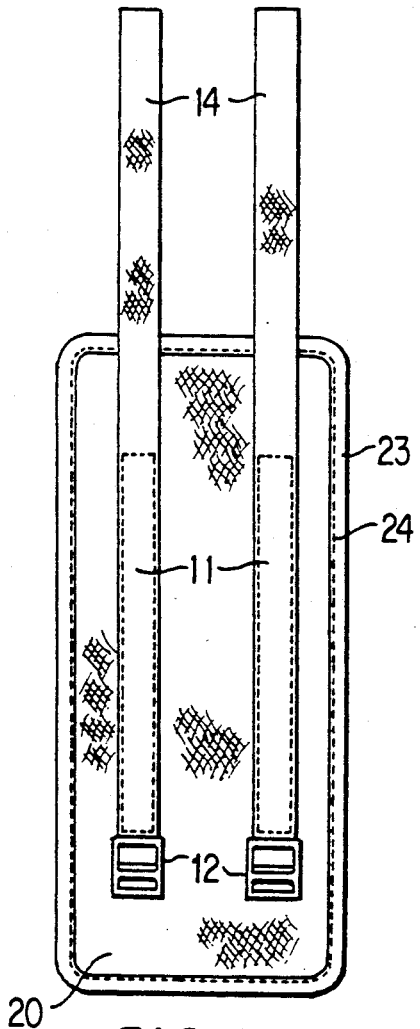
FIG. 2A is a view of the outside of the holder, showing strap-and-buckle fastening means and an optional, conventional timer.

FIG. 2A shows a flat view of the outer sheet 20 of the holder, to which fastening means comprising straps 11 and buckles 12 are securely attached. Although any suitable materials can be employed for the outer sheet, a preferred material for the outer sheet is polyurethane back-coated nylon pack cloth (400 dernier). The encircled "T" on the outer sheet represents a conventional timer, which is optionally present.

Figure 2B:
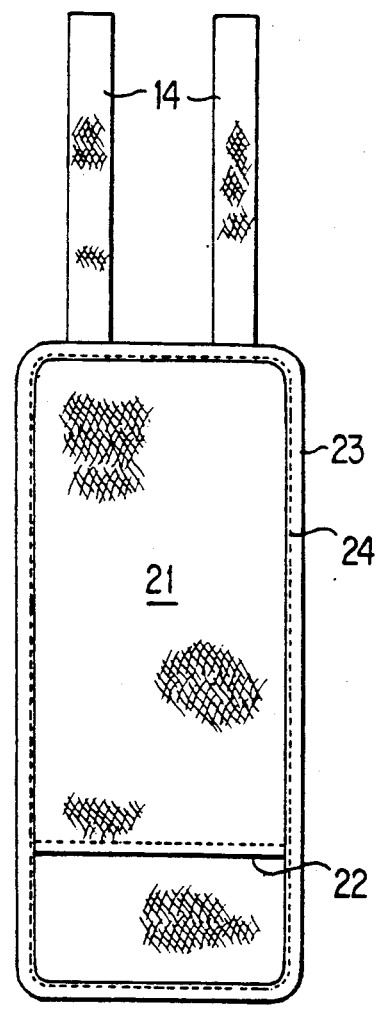
FIG. 2B is a view of the inside of the holder, showing the pocket into which the thermal compress is placed.

FIG. 2B shows an inner sheet 21, slightly shorter than outer sheet 10, forming a lip 22 of a "pocket". The preferred peripheral attachment means comprising edging material 23 and stitching 24 is also shown. Other peripheral attachment means can be employed, such as staples, rivets, glue or any combination of these means, either separately or with edging material 23 and stitching 24. Although any suitable materials can be employed, the preferred material to be employed for the edging material 23 is ⅞" nylon (gross grain ribbon), and the preferred material to be employed for the stitching 24 is #69 nylon (bonded and twisted; rot-resistant).

The outer surface area of the holder comprising the outer sheet 20 and edging material 23 (if present) can be from 6 inches long × 2 inches wide (6"×2", or 15 cm × 5 cm) to 24"×18" (60 cm × 45 cm).

One or more inner sheets of material 21 may be used, which may correspond to the number of thermal compresses used. Although any suitable materials can be employed for the inner sheet, the preferred material for the inner sheet(s) is ripstop nylon because of its durability and thinness, aiding both heat exchange to the affected body part during thermal treatment and minimizing heat exchange after the temperature of the kit is adjusted to the desired value and the kit is assembled. The surface area of the inner sheet(s) of material is from 6"×4" (15 cm × 10 cm) smaller to the same length and width as the outer sheet. The lip(s) of the pocket(s) can be aligned (parallel) either with the length or width of the holder.

The fastening means can comprise straps having a length of from 12 inches to 36 inches and a width of from ½ inch to 3 inches, and square or rectangular buckles made of plastic, metal, or both, having a crosspiece which forms two windows in the buckle, such as the design shown in FIG. 2A. Although any suitable materials can be used for the strap-and-buckle fastening means, the preferred material to be employed for the strap(s) is medium weight polypropylene, and the preferred buckle is a plastic buckle having a crosspiece which forms two windows, sold under the trademark of LADDER-LOC. Alternative fastening means can comprise two D-shaped loops made of metal or plastic; buckles similar to those shown in FIG. 2A, but having a second pivotally, centrally secured crosspiece, the straps then having corresponding eyelets; hook-and-loop fastening means (VELCRO), in which case, either (A) the straps can be secured to the outer surface of the holder as shown in FIG. 2A, and can be lengthened up to an additional 12" and widened up to the entire width of the holder; or (B) the outer sheet of the holder can be lengthened up to an additional 12" (for a total of 36" in length) and the hook-and-loop fastening means (VEL- CRO) can be attached to the inside of the outer sheet of the holder.

A preferred embodiment of the holder as shown in FIGS. 2A and 2B can further comprise a third sheet of material of the same dimensions as the outer sheet inserted between the inner and outer sheets, and a layer of insulating material between the outer sheet and the third sheet. Although any suitable materials can be employed for the third sheet and the insulating material, the preferred insulating material is expanded polyethylene foam (packing grade) having a thickness of 1/16" to 1", most preferably ¼" thick, and the preferred material for the outer sheet is polyurethane back-coated nylon pack cloth (400 dernier).

Four variations of the present thermal wrap kit are envisioned from the basic concept of the present invention. One variation is designed for the arm, elbow and ankle, a second for the knee and leg, a third for the wrist and hand, and a fourth for the shoulder. These designations of specific body parts are not limiting, since each variation can certainly be applied to body parts not specifically mentioned, such as the foot, head, torso, etc. It is also within the scope of the invention to employ these preferred variations interchangeably; i.e., the arm variation can be used for treatment of the knee, the wrist variation can be used on the arm of a child, etc.

The preferred variation for the arm has an outer sheet of material having dimensions of from 12"×4" (30 cm×10 cm) to 18"×8" (45 cm×20 cm), with particularly preferred dimensions of from 14"×6" (35 cm×15 cm) to 15"×7" (37.5 cm×17.5 cm). The inner sheet of material is preferably the same width and from 2.5" (6.2 cm) to 5" (12.5 cm) shorter than the outer sheet of material, a length of about 4" shorter than the outer sheet being particularly preferred. Preferred fastening means for the arm embodiment is strap-and-buckle, with strap dimensions preferably of from 16"×½" to 28"×2", with dimensions of from 18"×¾" to 22"×1" being particularly preferred, and the buckle is preferably that shown in FIG. 2A, preferably made of a high impact strength plastic. Although any number of fastening means can be employed, the preferred number for the arm embodiment is two.

The preferred embodiment for the knee has outer sheet dimensions of from 14"×8" (35 cm×20 cm) to 30"×15" (75 cm×37.5 cm), with particularly preferred dimensions of from 15"×10" (37.5 cm×25 cm) to 18"×14" (45 cm×35 cm). The preferred dimensions for the inner sheet are the same width as the outer sheet, and a length of from 2.5" (6.2 cm) to 5" (12.5 cm) shorter than the outer sheet, about 4" shorter (10 cm) being particularly preferred. Preferred fastening means are straps equipped with VELCRO fastening means. The straps preferably have dimensions of from 18"×1" (45 cm×2.5 cm) to 30"×3" (75 cm×7.5 cm), from 20"×1" (50 cm×2.5 cm) to 28"×2" (70 cm×5 cm) being particularly preferred. Any number of straps are effective, but two straps are preferred. Surface area of the patches of hook-and-loop fastening means (VELCRO) preferably have a width of from 1" (2.5 cm) less than to the same width as the straps, and are preferably from 2" (10 cm) to 8" (20 cm) in length. Any number of patches of hook-and-loop fastening means (VELCRO) can be employed; for example, two or three patches per strap. However, a single patch of hook-and-loop fastening means (VELCRO) is preferred.

The wrist embodiment has an outer sheet with dimensions preferably of from 8"×3" (20 cm×7.5 cm) to 12"×5" (30 cm×12.5 cm), with dimensions of from 9"×3" (22.5 cm×7.5 cm) to 11"×4" (27.5 cm×10 cm) being particularly preferred. The inner sheet preferably has the same width as the outer sheet, and a length preferably about 2" inches (5 cm) shorter than the outer sheet. Preferred fastening means are either strap-and-buckle means or straps equipped with hook-and-loop fastening means (VELCRO). A single strap having dimensions of from 12"×1" (30 cm×2.5 cm) to 16"×2" (40 cm×5 cm) is preferred for the wrist embodiment. The preferred buckle is of the design shown in FIG. 2A, and the preferred dimensions of the patches of hook-and-loop fastening means (VELCRO) are of from 2"×1" (5 cm×2.5 cm) to 4"×2" (10 cm×5 cm).

The shoulder embodiment has preferred dimensions of from 12"×8" (30 cm×20 cm) to 20"×16" (50 cm×40 cm), with dimensions of from 14"×12" (35 cm×30 cm) to 16"×14" (40 cm×35 cm) being particularly preferred. The inner sheet preferably has the same width as the outer sheet, and preferably has a length of from 0" to 3" (7.5 cm) shorter than that of the outer sheet. Preferred fastening means comprise a clamp employing a spring as a means for securing and applying pressure to the holder. Particularly preferred fastening means further comprise one or more elastic straps having a dimension of from 10"×0.25" (25 cm×0.6 cm) to 16"×2" (40 cm×5 cm) attached to the periphery of the holder such that the elastic straps run along the inner surface of the holder in a direction perpendicular to the straps shown in FIG. 2A (the width-wise direction).

Figure 3:
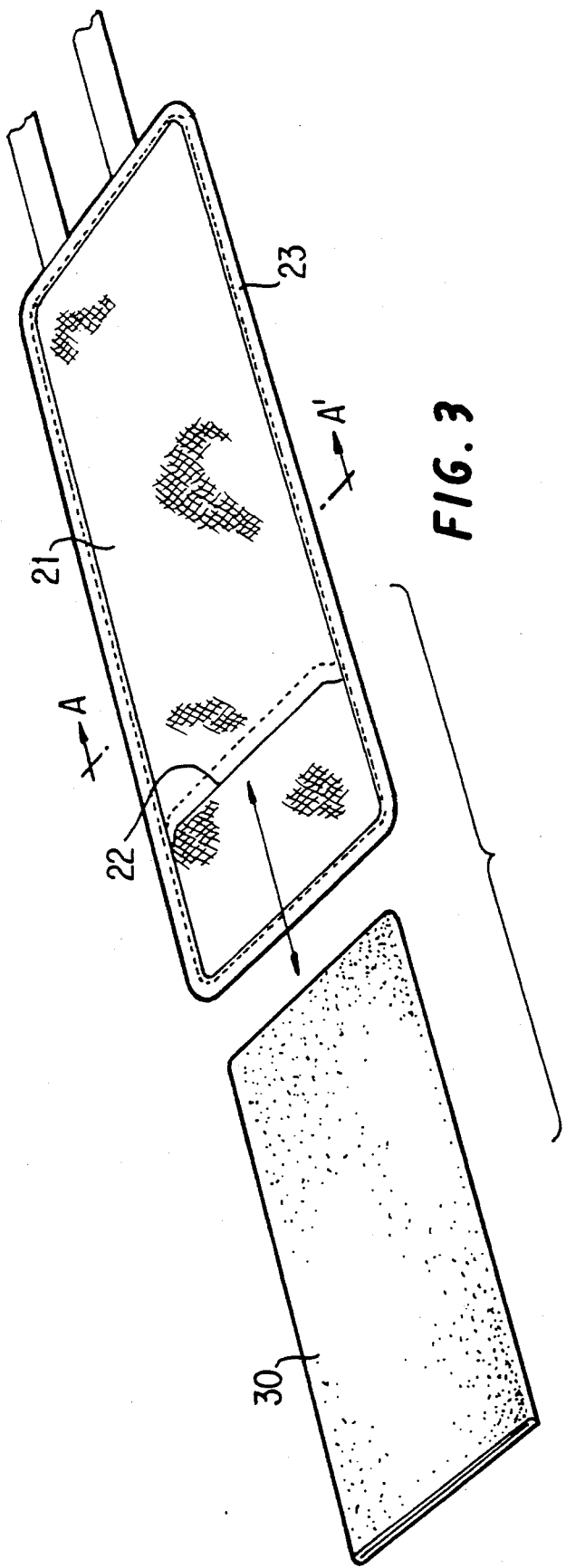
FIG. 3 shows the inside of the holder with the lip of the pocket raised, the thermal compress, and how the thermal compress is placed into or removed from the holder.

FIG. 3 shows the thermal compress 30, the inner surface of the holder, comprising inner sheet 21 and pocket lip 22, and how the thermal compress 30 is inserted into the holder. Suitable thermal compresses and materials comprising them are described in U.S. Pat. Nos. 4,856,651 (to Francis), 4,404,820 (to Romaine), 3,885,403 and 3,780,537 (to Spencer), and 3,545,230 (to Morse), all incorporated herein by reference, as well as many commercially available thermal compresses, such as those marketed by Physicians & Nurses Manufacturing Corporation (e.g., KOLD & HOT KOMPRESS [Catalog no. 730], Larchmont, N.Y.), Spenco Medical Corporation (e.g., SPENCO COLD WRAP; Waco, Tex.), Becton-Dickinson Company (e.g., ACE COLD COMPRESS #7516; Franklin Lakes, N.J.) and the Minnesota Mining and Manufacturing Company (COLDHOT PACK, St. Paul, Minn.). Particularly preferred thermal compresses are the KOLD & HOT KOMPRESS and the COLDHOT PACK. The dimensions of the thermal compress can be any such that the thermal compress fits inside the pocket of the holder, but preferred dimensions are those from 0.5" (1.2 cm) to 2" (5 cm) smaller than the area of the inner sheet of the holder. Alternatively, two or more thermal compresses can be employed, and means for separating the thermal compresses (such as multiple pockets) are preferably provided when multiple thermal compresses are employed. It is also within the scope of the present invention to provide means for overlapping the compresses slightly to provide more effective heat therapy or cryotherapy.

Figure 4:
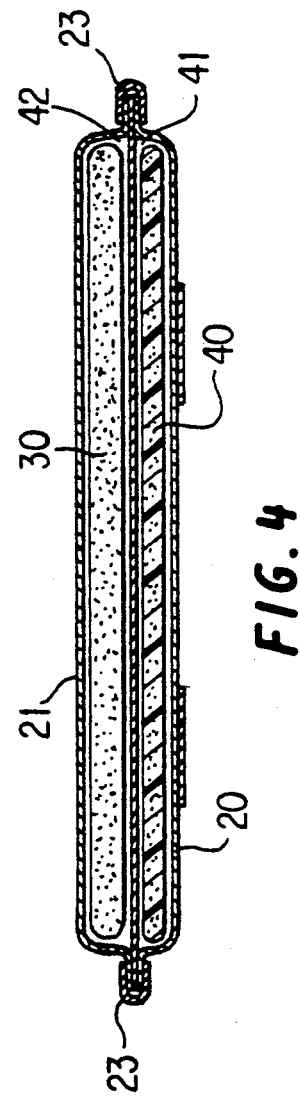
FIG. 4 shows a cross-sectional view of the holder containing the thermal compress.

FIG. 4 shows a cross-sectional view along the A—A' axis (shown in FIG. 3) of the thermal compress 30 inserted into a preferred embodiment of the holder 31 having insulation 40. The thermal compress 30 fills a pocket 42, the boundaries of which are defined by inner sheet 21 and middle sheet 41. The insulation 40 is between outer sheet 20 and third (middle) sheet 41. The three sheets are peripherally attached to each other by use of edging material 23 and stitching (not shown). Straps 11 are attached to the outer sheet 20.

Figure 5:
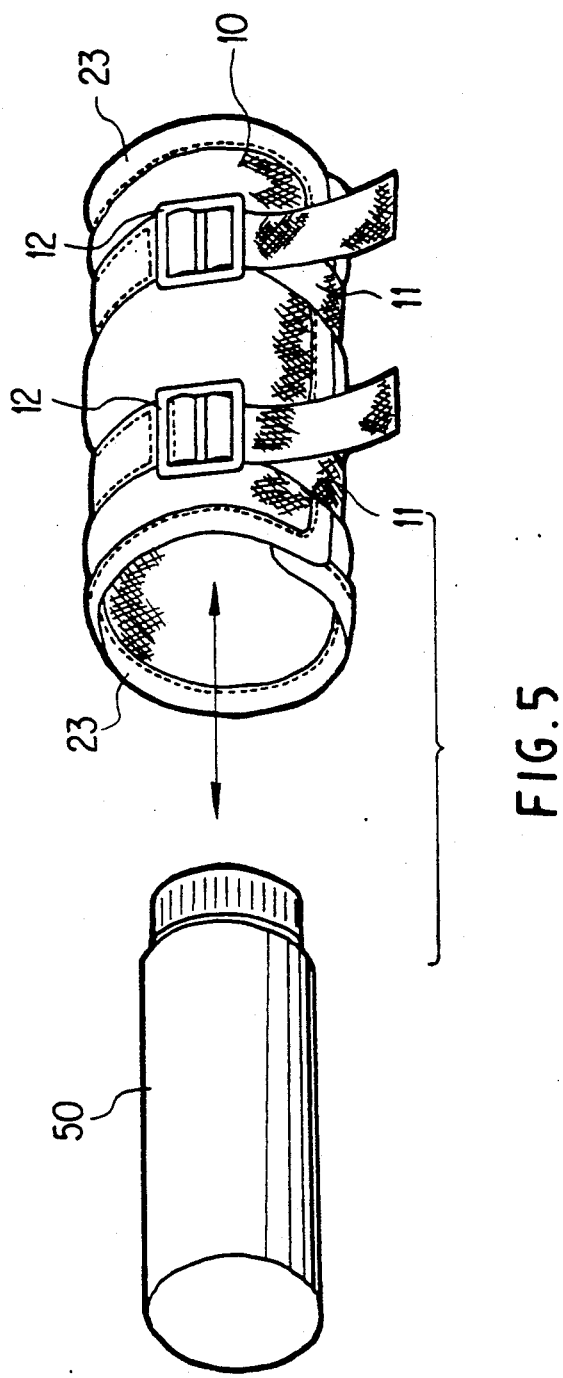
FIG. 5 shows a container, the outside of the holder containing the thermal compress (not seen) in a securable arrangement, and how the holder containing the thermal compress fits around the container as well as how the holder containing the thermal compress is removed from the container.

FIG. 5 shows the interaction between container 50 and holder 10 containing the thermal compress (not shown). Fastening means comprising straps 11 and buckles 12 are shown in the manner required for securing the holder 10 to an object (e.g., the container or a body part). The container 50 slides into or out from the holder 10 while the holder is in a securable arrangement. For cryotherapy, the container is preferably a wide-mouth bottle made of high-density polyethylene, but any cylindrical object can be used which is:

(A) capable of containing a substance that is liquid at 25° C.,
(B) which can withstand the temperatures of therapeutic treatment, and
(C) can be inserted into the holder containing the thermal compress, then allow the assembled holder, thermal compress, and container to fit into the insulated bag.

Examples of such cylindrical objects are glass and plastic bottles of soft drinks, juices, water, beer, or other beverages; cans of such beverages; etc. The preferred size of the polyethylene bottle of the arm variation of the present thermal wrap kit is 500 ml (16 oz.), but larger sizes (such as 1000 ml or 32 oz.) can be used for the larger variations (knee and shoulder), and smaller sizes (such as 250 ml or 8 oz.) can be used for smaller variations (such as the wrist). For heat therapy, the polyethylene bottle can be used, or alternatively, an appropriately shaped solid object able to hold heat as well or better than water (such as a stone) can be substituted for the container. Preferably, the length of the container 50 does not allow it to extend more than 1" (2.5 cm) in either direction beyond the edging material 23 (or similar boundary) of the holder 10.

Figure 6:
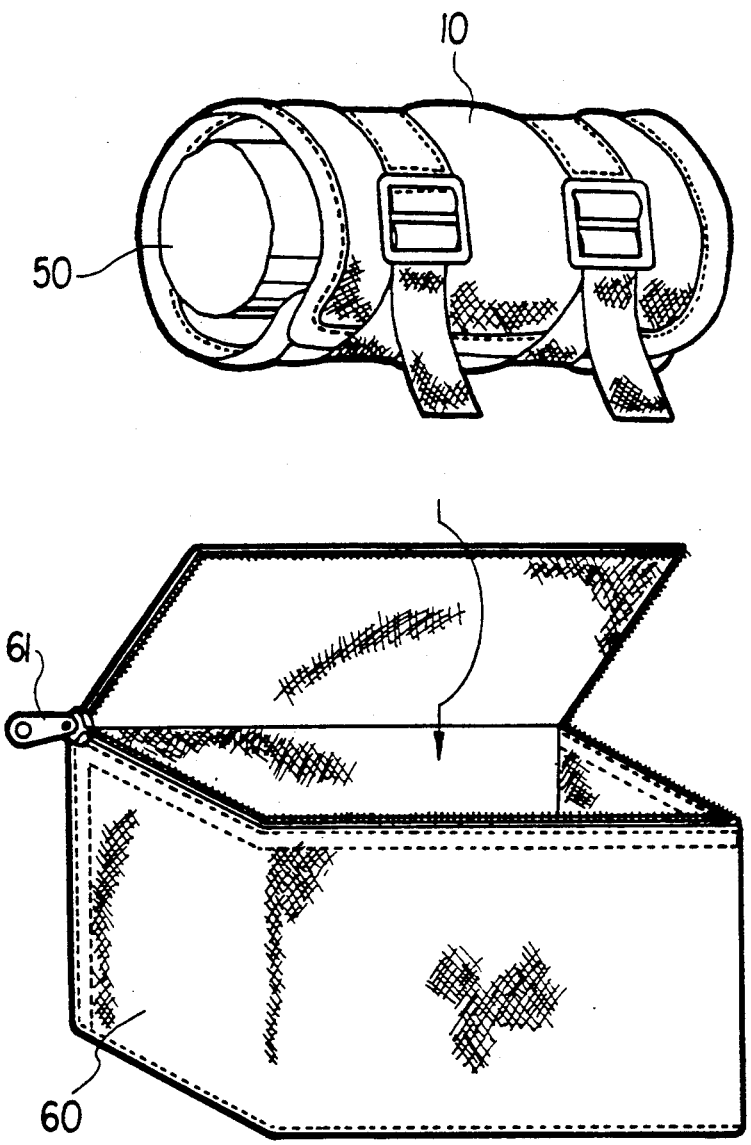
FIG. 6 shows an insulated bag equipped with zipper sealing means and the assembled holder, thermal compress (not seen) and container, and how the assembled holder, thermal compress and container fit inside the insulated bag, thus forming the invention therapeutic thermal wrap kit.
Figure 7A:
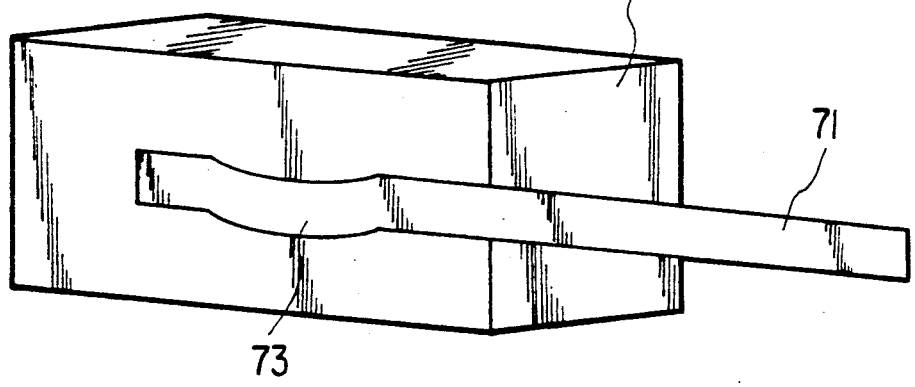
FIG. 7A is a top view of an insulated bag having sealing means comprising foldable flaps and a strap equipped with hook-and-loop fastening means (such as that sold under the trademark VELCRO)
Figure 7B:
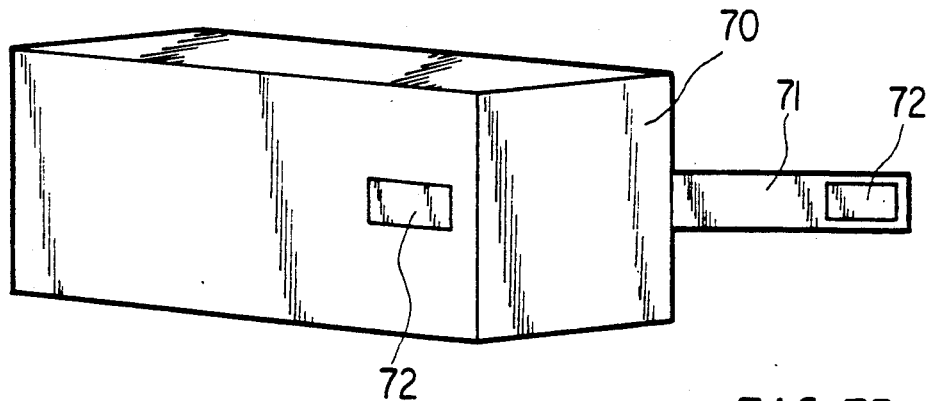
FIG. 7B is a bottom view of the insulated bag having sealing means comprising foldable flaps and a strap equipped with hook-and-loop fastening means.
Figure 7C:
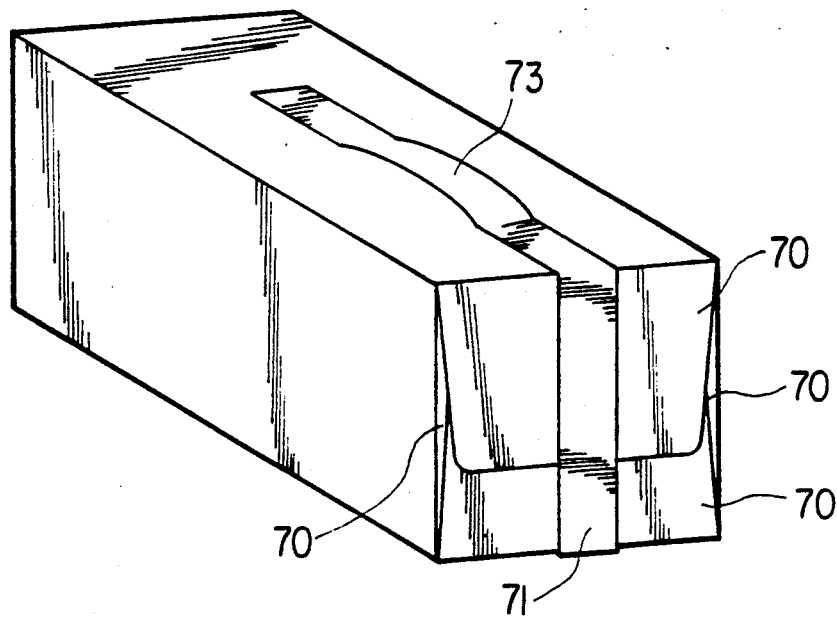
FIG. 7C is a corner view of the insulated bag having sealing means comprising foldable flaps and a strap equipped with hook-and-loop fastening means in a secured arrangement.
Figure 8:
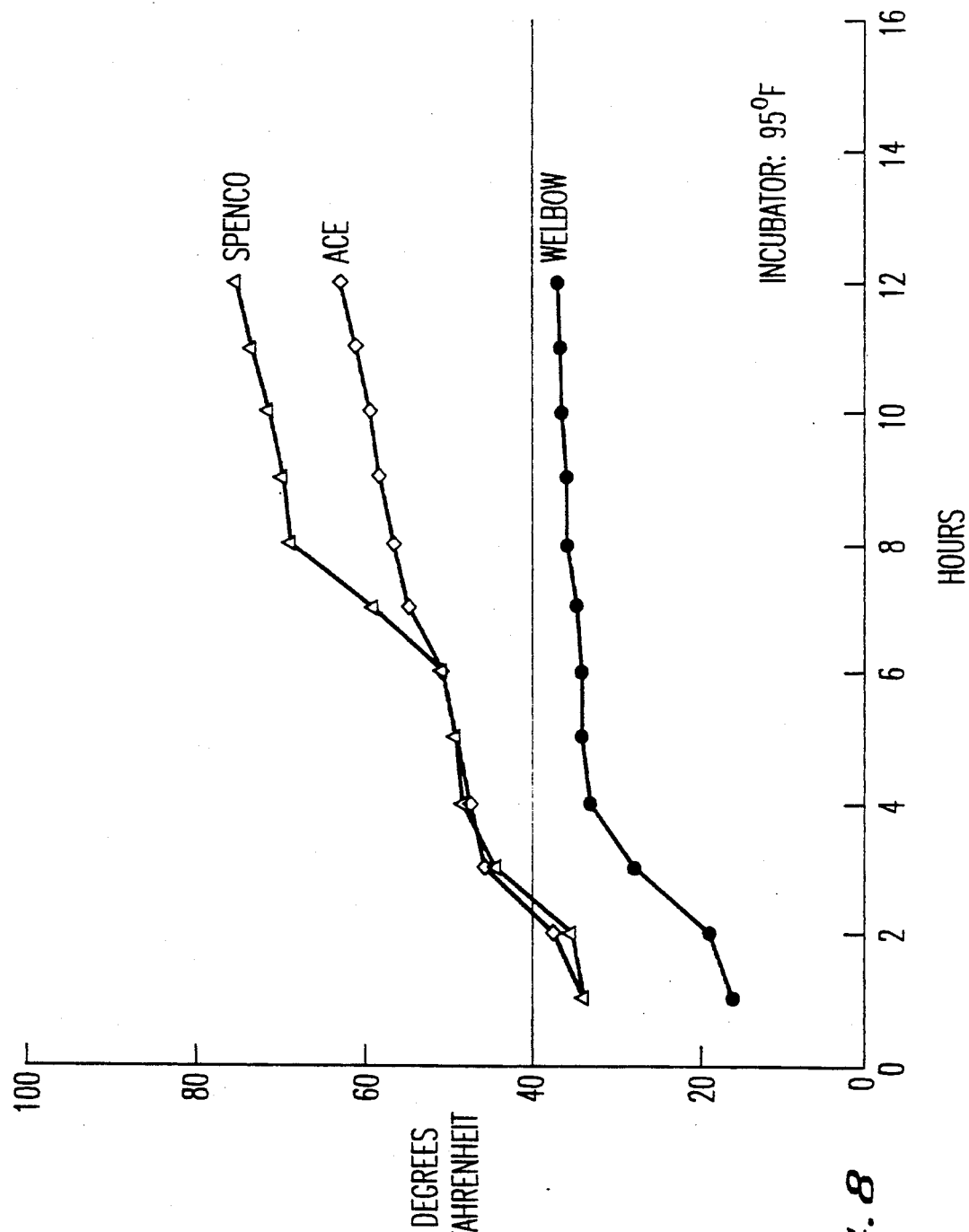
FIGS. 8 and 9 are graphs plotting the temperatures inside the present therapeutic thermal wrap kit (WELBOW) and similar assemblies of the closest commercially available components, wherein each kit or assembly was cooled and incubated simultaneously under identical conditions, for comparative purposes.

FIG. 6 shows the assembled container 50, holder 10, and thermal compress (not seen), and their interaction with the insulated bag 60. The insulated bag 60 can have any dimensions allowing the assembled container 50 and holder 10 containing the thermal compress to fit inside, but the preferred dimensions are such that the length, width and height inside the insulated bag are no more than 2" (5 cm) longer than the height and diameter of the assembled container 50 and holder 10 containing the thermal compress. The insulated bag 60 can be equipped with sealing means comprising a zipper 61, or it can comprise from one to four flaps securable with hook-and-loop fastening means (VELCRO). Alternatively, the hook-and-loop fastening means can be secured to one or more straps attached to the outside of the insulated bag 60. The preferred sealing means, exemplified in FIGS. 7A, 7B and 7C comprises four flaps 70 at an end of the insulated bag having the smallest dimensions (an end defined by height and width), each flap 70 foldable over another such that the flaps overlap, secured by one or more straps 71 equipped with hook-and-loop fastening means 72 (VELCRO). The strap(s) are permanently attached to one outside surface of the insulated bag, lie across the folded flaps, and are reversibly attached to the opposite outside surface by hook-and-loop fastening means (VELCRO) as shown in FIG. 7C. Optionally, the strap(s) can form a D-shaped handle 73 by permanently attaching the strap(s) to one outside surface in two places 4" to 12" apart, such that 0.5" to 4" additional length is provided to the strap(s) in relation to the corresponding sites of attachment, thus providing an insulated carrying bag.

FEATURES AND ADVANTAGES OF THE INVENTION

One advantage of this invention to the user is that it allows him/her to take partial control of his/her own medical treatment, an accepted theory in modern sports medicine. Players who have a tendency to suffer from muscle and/or ligament stress (for example, tennis elbow or chronic knee problems) can easily and adequately plan in advance to provide for a thermal wrap to be applied both during exercise and immediately thereafter.

The temperature of the present therapeutic thermal wrap kit is easily adjusted to a therapeutically effective temperature, and further, is able to maintain the therapeutically effective temperature for a period of time unexpectedly and surprisingly longer than any such device or assembly of devices currently available. The present therapeutic thermal wrap kit, after prior cooling to −15° F. (26° C.) has been proven to maintain a temperature of less than 40° F. (4.4° C.) for seventeen hours in an 86° F. (30° C.) incubator. It is thought that 40° F. (4.4° C.) or less is a therapeutically effective temperature for cryotherapy (literature accompanying the COLDHOT PACK manufactured by Minnesota Mining and Manufacturing Company, St. Paul, Minn., incorporated herein by reference), and by extrapolation of the graphed results shown in FIG. 10, the invention therapeutic thermal wrap kit should be able to maintain a therapeutically effective temperature for at least 24 h at 86° F.

The surprisingly long maintenance of therapeutic effectiveness displayed by the present kit, as well as the kit's compact design, enables and greatly enhances portability. The ease of portability of the present kit is an unexpected advantage over prior thermal wraps. For example, the user can transport the present therapeutic thermal wrap to remote exercise site over the course of several hours, participate in physical activities over the next several hours, then use the present wrap immediately after the physical activity while the wrap is still at a therapeutically effective temperature. The user could conceivably take the present kit to work, leave the kit in a car, locker or desk all day, then participate in up to 2-3 h of exercise after an 8-hour workday, and still be able to use the present wrap while at an effective temperature for cryotherapy.

To use the present thermal wrap kit for cryotherapy, one simply fills the empty container with a liquid (such as tap water) to a level slightly below the top of the container, seals the container, assembles the thermal wrap kit as instructed above, then places the assembled kit overnight in a freezer, such as those typically found in commercially available freezers and refrigerator-freezers. Alternatively, the thermal compress and the sealed container with liquid can be placed in a freezer for 2-4 h or more, then the present thermal wrap kit is assembled. Both methods (and variants in between) provide a portable, effective cryotherapeutic kit which will maintain an effective temperature of less than 40° F. (4.4° C.) for at least 10 h.

For heat treatment, one can heat the thermal compress in boiling water for 10 min or more, place it in the holder, fill the container with the boiling water, seal the container, and assemble the thermal wrap kit as instructed above. Optionally, a solid heat retaining object such as a stone can be heated to a desired temperature, and substituted for the container filled with hot water above. Alternatively, many commercially available thermal compresses (for example, the HOT & KOLD KOMPRESS sold by Physicians & Nurses Manufacturing Corporation, Larchmont, N.Y. and the COLDHOT PACK manufactured by Minnesota Mining and Manufacturing Company, St. Paul, Minn.) can be heated by means of a microwave oven, which is also effective for heating a non-metal container of liquid. Another means of thermally adjusting the temperature of the compress is to employ a chemically activated compress.

When needed, the holder containing the thermal compress and the container is taken from the insulated bag. The holder fastenings are easily loosened, the container taken out, and the holder containing the thermal compress is applied to the injured body part. The holder and thermal compress conform easily to the injured body part because the thermal compress remains pliable at all therapeutically effective temperatures.

If the injury is severe enough to immobilize an arm and/or hand, the holder can be fastened and unfastened with only one hand.

The present thermal wrap kit maintains a therapeutically effective temperature for an unexpectedly long period of time because of the synergy of the four essential elements:
(a) the holder;
(b) the thermal compress;
(c) the container; and
(d) the insulated bag.

The cylindrical shape of the assembled holder, thermal compress and container minimizes heat loss or gain by minimizing the surface area-to-volume ratio. The close fit of the preferred insulated bag to the assembled components as well as the complete contact of the container and thermal compress (separated by only the inner sheet of the holder) further minimizes this type of heat loss or gain, and prevents air circulation around and through the assembly, even further maximizing the synergy of the essential elements.

The present therapeutic thermal wrap kit can be effectively used for different body parts such as ankles, knees, feet, and the like. For the head, shoulder, torso, etc., the holder and thermal compress can be used as a cold massage and can be used effectively on any body part by this method. For example, some doctors such as Kraus ("Sports Injuries," Playboy Press, 1981) discuss the use of "ice massage." He states that rubbing ice back and forth over the injured area is a more therapeutic means of treating injury than just applying a cold pack.

With the thermal compress used as a massage, it can be an emergency treatment for animals, and young children, and for any injuries where swelling and/or accompanying pain, i.e., insect bites, have to be brought under control by the use of cold. Consequently, the holder and thermal compress of the present invention have broader applicability and do not necessarily have to be used as part of the therapeutic thermal wrap kit.

Likewise, for therapies requiring use of heat, such as muscle strains or even frostbite, the holder and thermal compress can be effective as a type of heat massage or heating pad.

A small conventional timer on the holder is an option. This timing device could be an advantage and convenience for players who want to apply the thermal treatment for a certain specified number of minutes, and thus, insure optimal use. A optional built-in alarm or bell alerts the user when to remove the holder and compress.

Another advantage of the invention is that the bottle or container can be used for a variety of liquids such as water, juice, and soft drinks. This liquid can then be consumed to slake thirst and prevent dehydration. Alternatively, as a means of further slowing heat exchange time, the container can be filled with an alternative substance, such as a saline (salt) solution or an ethylene glycol solution.

The present invention can be reused many times over a long period of time, and users will be able to rely on an easy, compact, rugged, inexpensive, and reliable means of dealing with muscle discomfort and other similar injuries.

Having generally described this invention, a further understanding can be obtained by reference to certain specific examples which are provided herein for purposes of illustration only and are not intended to be limiting unless otherwise specified.

EXAMPLE 1

A 500 ml (16 oz.) high density polyethylene bottle having a wide-mouth screw top was filled with tap water to about 1 inch below its top, and the cap was screwed on tightly. A thermal compress measuring 9.5"×4" (the COLDHOT PACK manufactured by the Minnesota Mining and Manufacturing Company, St. Paul, Minn.) was placed in a holder of outer surface dimensions of 15"×6.5" equipped with an insulated layer, two strap-and-buckle fastening means and a ripstop nylon inner sheet member having dimensions of 11"×6.5". The holder containing the thermal compress was secured around the polyethylene bottle, and the assembly was placed inside an insulated bag having dimensions of 8"×5.5"×5.5" equipped with four folding flaps at one end area 5.5"×5.5", secured by a 1" wide strap equipped of with hook-and-loop fastening means, along with a dial thermometer, the stem of which was placed between the container and the inner sheet of the holder such that the dial was easily seen when the flaps of the insulated ( bag were opened. The thermal wrap kit was then cooled to about −20° C. and transported over the course of 1 h to an incubator. The incubator was maintained at 35° C. (95° F.) during the course of the experiment. Hourly temperature measurements were taken. The results are presented in Table 1 and graphically in FIG. 9. After 1 h transportation time, the present thermal wrap kit required nearly 4 h in the 35° C. incubator to reach 0° C., and after 10 h in the incubator, the temperature inside the present thermal wrap kit had risen to only 2.2° C.

TABLE 1

| | Temperature (°C.) | | | | | | | | | | |
|---|---|---|---|---|---|---|---|---|---|---|---|
| | Time (h) | | | | | | | | | | |
| | 1* | 2 | 3 | 4 | 5 | 6 | 7 | 8 | 9 | 10 | 11 |
| Present Example #1 | −9 | −8 | −2 | 1 | 1 | 1 | 1.5 | 2 | 2 | 2.2 | 2.2 |

TABLE 1-continued

| | Temperature (°C.) Time (h) | | | | | | | | | | |
|---|---|---|---|---|---|---|---|---|---|---|---|
| | 1* | 2 | 3 | 4 | 5 | 6 | 7 | 8 | 9 | 10 | 11 |
| Present Example #2 | −10 | −7 | −3 | 0 | 1 | 1 | 1.2 | 2 | 2 | 2.5 | 2.5 |
| Comparative Example #1 | 1 | 2 | 7 | 9 | 9.5 | 10.5 | 15 | 20.5 | 21 | 22 | 23 |
| Comparative Example #2 | 1 | 3 | 7.5 | 8.5 | 9.5 | 10.2 | 12.5 | 13.5 | 14.5 | 15 | 16 |

*The first hour was transportation time to the incubation site.

EXAMPLE 2

The experiment in Example 1 was repeated, substituting another commercially available thermal compress (ACE COLD COMPRESS #7516, manufactured by the Becton Dickenson Company, Franklin Lakes, N.J.) for the thermal compress of Example 1, with similar results, also presented in Table 1 and FIG. 7 (FIG. 7 plots the average value of the temperature inside the kits of Examples 1 and 2). The horizontal line at 40° F. indicates the maximum therapeutically effective temperature for cryotherapy. After 4 h in the incubator, the temperature inside the kit was exactly 0° C.; after 10 h in the incubator, the temperature was 2.5° C.

COMPARATIVE EXAMPLE 1

A commercially available thermal compress/holder assembly having a terry cloth covering (SPENCO COLD WRAP, manufactured by Spenco Medical Corporation, Waco, Tex.) was first secured around a commercially available ice substitute (COLEMAN CHILLER, 20 oz, 625 ml, manufactured by Coleman Company, Wichita, Kans.), then soaked in water and placed inside a commercially available insulated bag (LETCHNERS INSULATED LUNCH TOTE) with a dial thermometer. The experiment of Example 1 was repeated, and the results are presented in Table 1 and FIG. 7. The temperature inside the kit had already risen above 0° C. during only the transportation time, and within 2 h inside the incubator, the kit of Comparative Example 1 was already therapeutically ineffective (the temperature had risen above 4.4° C.). After 10 h in the incubator, the temperature inside the insulated bag had risen to 23° C.

COMPARATIVE EXAMPLE 2

The experiment of Comparative Example 1 was repeated, substituting the thermal compress of Example 2 (ACE COLD COMPRESS #7516) and a commercially available elastic wrap bandage (ACE BANDAGE, manufactured by the Becton Dickenson Company, Franklin Lakes, N.J.) for the thermal compress/holder assembly. The thermal compress was secured to the ice substitute by use of rubber bands. The results are shown in Table 1 and FIG. 7. Similar to Comparative Example 1, the temperature inside the kit of Comparative Example 2 had risen above 0° C. during the transportation time, and the comparative kit had become therapeutically ineffective within 2 h (the temperature had become greater than 4.4° C.). After 10 h in the incubator, the temperature had risen to 16° C.

EXAMPLE 3

The experiment of Example 1 was repeated with the following changes:
A) a different thermal compress (HOT & KOLD KOMPRESS, manufactured by Physicians and Nurses Manufacturing Corporation, Larchmont, N.Y.) was substituted for the thermal compress of Example 1;
B) the thermal wrap kit was cooled to −15° F. (−26° C.) before the start of the experiment;
C) no transportation time to the incubation site was necessary; and
D) the incubator was maintained at 86° F. (30° C.).

Figure 9:
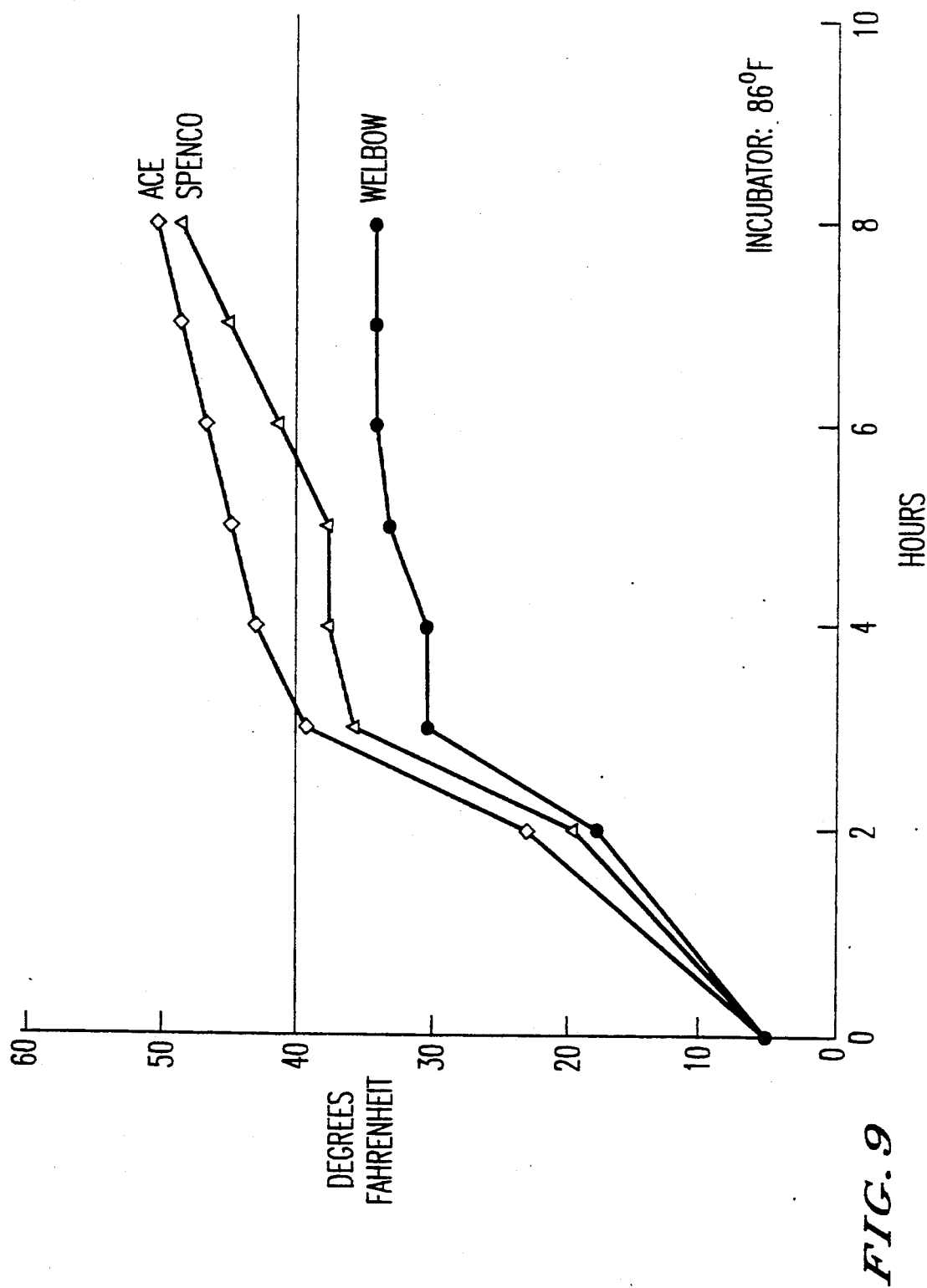

The results are displayed in Table 2 and FIG. 9. The horizontal line at 40° F. indicates the maximum therapeutically effective temperature for cryotherapy. The kit of Example 3 not only maintained a cryotherapeutically effective temperature for 8 h, but had a temperature of about the freezing point of water after 8 h incubation.

COMPARATIVE EXAMPLES 3 AND 4

The thermal wrap kits of Comparative Examples 1 and 2 were employed in the experiment of Example 3, respectively. Results are displayed in Table 2 and FIG. 9. The kit of Comparative Example 3 (denoted SPENCO in FIG. 9) maintained cryotherapeutic effectiveness for between 5 and 6 h, and the kit of Comparative Example 4 (denoted ACE in FIG. 9) maintained cryotherapeutic effectiveness for between 3 and 4 h.

TABLE 2

| | Temperature (°F.) Time (h) | | | | | | | |
|---|---|---|---|---|---|---|---|---|
| | 0 | 2 | 3 | 4 | 5 | 6 | 7 | 8 |
| Present Example #3 (WELBOW) | 5 | 17.6 | 30.2 | 30.2 | 32.9 | 33.8 | 33.8 | 33.8 |
| Comparative Example #3 (SPENCO) | 5 | 19.4 | 35.6 | 37.4 | 37.4 | 41 | 44.6 | 48.2 |
| Comparative Example #4 (ACE) | 5 | 23 | 39.2 | 42.8 | 44.6 | 46.4 | 48.2 | 50 |

EXAMPLE 4 AND COMPARATIVE EXAMPLES 5–7

Figure 10:
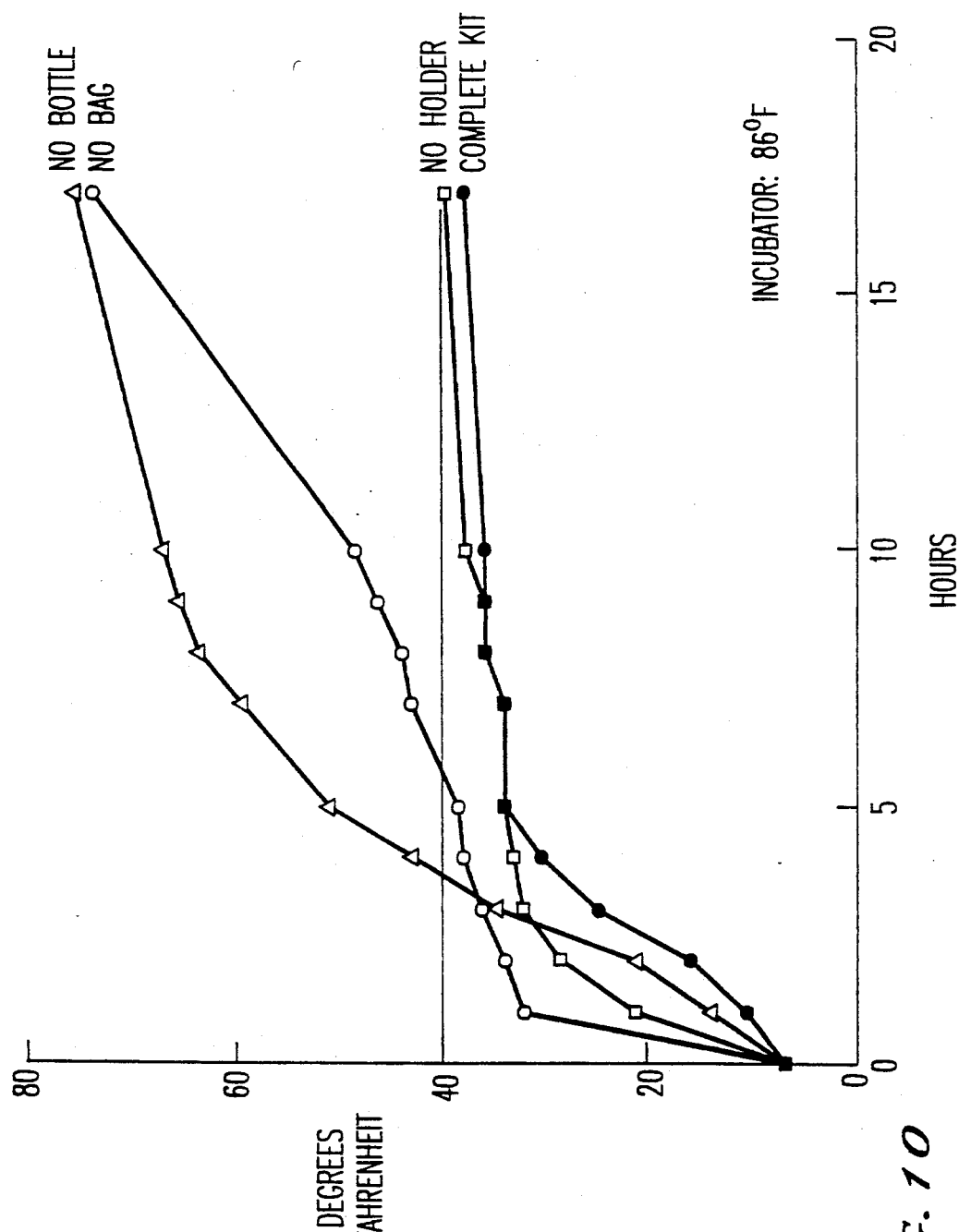
FIG. 10 is a graph plotting the temperature of assemblies of essential components of the invention therapeutic thermal wrap kit such that each assembly tested contained only three of the four essential components, as compared to the invention therapeutic thermal wrap kit.

The experiment of Example 3 was repeated four times, and three of those times, one essential component was omitted:
EXAMPLE 4: Complete kit
Comparative Example 5: No container (bottle)
Comparative Example 6: No (insulated) bag
Comparative Example 7: No holder The results are displayed in Table 3 and FIG. 10. The horizontal line at 40° F. indicates the maximum therapeutically effective temperature for cryotherapy. It is important to note that the results displayed in FIG. 10 show the criticality of the insulated bag and the container of the present kit. Removal of the essential insulated bag from the kit resulted in the kit losing its cryotherapeutic effectiveness after only between 6 and 7 h, and removal of the essential container from the kit resulted in the kit losing its cryotherapeutic effectiveness after only between 3 and 4 h.

TABLE 3

| | Temperature (°F.) | | | | | | | | | | |
|---|---|---|---|---|---|---|---|---|---|---|---|
| | Time (h) | | | | | | | | | | |
| | 0 | 1 | 2 | 3 | 4 | 5 | 7 | 8 | 9 | 10 | 17 |
| Present Example #4 (Complete Kit) | 6.8 | 10.4 | 15.8 | 24.8 | 30.2 | 33.8 | 33.8 | 35.6 | 35.6 | 35.6 | 37.4 |
| Comparative Example #5 (No Bottle) | 6.8 | 14.0 | 21.2 | 34.7 | 42.8 | 50.9 | 59.0 | 63.3 | 65.3 | 66.7 | 75.2 |
| Comparative Example #6 (No Bag) | 6.8 | 32.0 | 33.8 | 36.0 | 37.8 | 38.3 | 42.8 | 43.7 | 46.0 | 48.2 | 73.4 |
| Comparative Example #7 (No Holder) | 6.8 | 21.2 | 28.4 | 32.0 | 32.9 | 33.8 | 33.8 | 33.8 | 35.6 | 37.4 | 39.2 |

Having now fully described the invention, it will be apparent to one of ordinary skill in the art that many changes and modifications can be made thereto without departing from the spirit or scope of the invention as set forth herein.

I claim:

1. A therapeutic thermal wrap kit, comprising:
   (A) a holder comprising
      (1) at least two sheets of material peripherally attached to each other, said sheets forming a pocket, and
      (2) adjustable fastening means provided on the outside of said holder, sufficiently long to secure said holder to an affected body part;
   (B) a thermal compress, which is inserted into said pocket;
   (C) a container, around which the holder containing the thermal compress is placed, said container providing a means by which a therapeutically effective temperature can be maintained for at least eight hours at 86° F.; and
   (D) an insulated bag, into which the assembled holder, thermal compress and container are placed.

2. The therapeutic thermal wrap kit of claim 1, said container providing a means by which a therapeutically effective temperature can be maintained for at least seventeen hours at 86° F.

3. The therapeutic thermal wrap kit of claim 1, said container providing a means by which a therapeutically effective temperature can be maintained for at least eleven hours at 95° F.

4. The therapeutic thermal wrap kit of claim 1, said container containing a substance, said substance comprising a commercially available beverage.

5. The therapeutic thermal wrap kit of claim 1, further comprising a timer attached to the outside of said holder.

6. The therapeutic thermal wrap kit of claim 1, further comprising a timer attached to the outside of said insulated bag.

7. The therapeutic thermal wrap kit of claim 1, said fastening means comprising at least one strap and at least one buckle, said strap having an end comprising a loop to which said buckle is attached.

8. The therapeutic thermal wrap kit of claim 7, said fastening means comprising at least two straps and at least two buckles, said straps each having an end comprising a loop to which each of said buckles is attached.

9. The therapeutic thermal wrap kit of claim 1, said fastening means comprising at least one strap provided with hook-and-loop fastening means.

10. The therapeutic thermal wrap kit of claim 1, at least one of said sheets comprising polyurethane back-coated nylon pack cloth (400 dernier).

11. The therapeutic thermal wrap kit of claim 1, at least one of said sheets comprising ripstop nylon.

12. The therapeutic thermal wrap kit of claim 1, said holder further comprising a third sheet of material and an insulating material placed between two of said sheets.

13. The therapeutic thermal wrap kit of claim 12, at least two of said sheets comprising polyurethane back-coated nylon pack cloth (400 dernier) and said insulating material comprising expanded polyethylene foam (packing grade).

14. The therapeutic thermal wrap kit of claim 1, said insulated bag comprising polyurethane back-coated nylon pack cloth (400 dernier) and insulating material comprising expanded polyethylene foam (packing grade) and sealing means.

15. The therapeutic thermal wrap kit of claim 14, said sealing means being selected from the group consisting of a zipper and one or more straps having hook-and-loop fastening means.

16. The therapeutic thermal wrap kit of claim 1, said container comprising a high density polyethylene wide-mouth bottle.

17. A method for the treatment of body discomfort, comprising the sequential steps of:
   (A) adjusting the temperature of a thermal compress and a container containing a substance to a temperature of from −20° to 120° C., said substance being liquid at 25° C.;
   (B) placing said thermal compress in a holder comprising
      (1) at least two sheets of material peripherally attached to each other, said sheets forming a pocket, and
      (2) fastening means attachable to the outside of said pocket;
   (C) securing said holder containing said thermal compress around said container;
   (D) placing said secured holder in an insulated bag, forming a therapeutic thermal wrap kit;
   (E) removing said secured holder from said insulated bag;
   (F) separating said secured holder from said container; and (G) securing said holder containing said thermal compress to a body part experiencing discomfort.

18. The method of claim 17, wherein step (B) is the first step, and step (A) is performed after step (C).

19. The method of claim 17, wherein step (B) is the first step, and step (A) is performed after step (D).

20. The method of claim 17, further comprising transporting said therapeutic thermal wrap kit to a remote location prior to removing said secured holder from said insulated bag.

21. The method of claim 17, further comprising allowing a period of time of from 2 to 10 hours elapse after said forming said therapeutic thermal wrap kit and prior to removing said secured holder from said insulated bag.

22. The method of claim 17, further comprising timing the duration of use of said holder containing said thermal compress after securing to said body part.

* * * * *